United States Patent [19]

Ishibashi et al.

[11] 4,272,156
[45] Jun. 9, 1981

[54] ILLUMINATION OPTICAL SYSTEM USING OPTICAL FIBER BUNDLES

[75] Inventors: Kuniaki Ishibashi, Omiya; Norio Shiraishi; Susumu Oshiro, both of Iwatsuki, all of Japan

[73] Assignee: Fuji Photo Optical Co., Ltd., Saitama, Japan

[21] Appl. No.: 949,629

[22] Filed: Oct. 10, 1978

[30] Foreign Application Priority Data

Dec. 27, 1977 [JP] Japan .................. 52-158119

[51] Int. Cl.³ ............................................... G02B 5/17
[52] U.S. Cl. ......................... 350/96.26; 350/96.24
[58] Field of Search ............ 350/96.24, 96.25, 96.26, 350/96.10

[56] References Cited

U.S. PATENT DOCUMENTS

| | | | |
|---|---|---|---|
| 2,843,112 | 7/1958 | Miller | 350/96.26 |
| 3,494,354 | 2/1970 | Yokota et al. | 350/96.26 |
| 3,533,657 | 10/1970 | Da Silva | 350/96.24 |
| 3,874,783 | 4/1975 | Cole | 350/96.24 |
| 3,956,587 | 5/1976 | Nelson | 350/96.24 |

*Primary Examiner*—Stewart J. Levy
*Attorney, Agent, or Firm*—Harold L. Stults; Pasquale A. Razzano

[57] ABSTRACT

An illumination optical system using optical fiber bundles. The optical fiber bundles are assembled to form an illumination optical system. The exit end faces of the fiber bundles are flat and inclined in different directions to effect a diverging illumination light flux as a whole.

7 Claims, 8 Drawing Figures

ILLUMINATION OPTICAL SYSTEM USING OPTICAL FIBER BUNDLES

BACKGROUND OF THE INVENTION

1. Field of the Invention

This invention relates to an improvement in an illumination system using optical fiber bundles, and more particularly to the expansion of the numerical aperture in an optical fiber bundle used for instance in an endoscope.

2. Description of the Prior Art

In an endoscope or the like in which optical fiber bundles are used for illuminating and viewing the interiors of intestines or the inside structures of instruments, illumination light is guided through an optical fiber bundle from an outside light source and is distributed to illuminate the object to be viewed at an end of the bundle. The area illuminated by the illumination light emitted from the end of the optical fiber bundle is determined by the numerical aperture (N.A.) thereof which is represented by the following formula $$N.A. = (n_1^2 - n_2^2)^{\frac{1}{2}}$$

where $n_1$ is the refractive index of the core of the fiber and $n_2$ is the refractive index of the fiber cladding. The numerical aperture (N.A.) is usually about 0.5 and the angle of the extreme meridional ray trapped in a fiber is about 60°. This means that the illumination light emitted from the end of the optical fiber bundle has a distribution angle of about 30° which is the half angle of the cone of light at the exit of the optical fiber bundle.

An expanded distribution angle of illumination light is sometimes desired so as to make it possible to obtain a broader area of illumination on the object and enable observation and photographing of the object with a wider field of view.

In order to expand the distribution angle of illumination light of the optical fiber bundle, it has been suggested to make the exit end face of the bundle convex or concave as disclosed in Japanese Utility Model Publication No. 10346/1977 issued Mar. 5, 1977. However, an optical fiber bundle having the convex or concave exit end face is very difficult to produce.

SUMMARY OF THE INVENTION

The object of the present invention is to provide an optical fiber bundle illumination system having an expanded numerical aperture which can easily be produced.

The optical fiber bundle illumination system in accordance with the present invention is characterized in that the exit end faces of the optical fiber bundles are obliquely cut and finished. The exit end face of each optical fiber bundle used in the illuminating system is flat and inclined at an angle with respect to a plane normal to the axes of fibers of the fiber bundle.

DESCRIPTION OF THE PREFERRED EMBODIMENTS

Now an embodiment of the present invention will be described in detail with reference to FIG. 1. A focusing lens 1 and an image guide optical fiber bundle 2 constitute an observation system, and optical fiber bundles 3 and 4 surrounding the observation system constitute an illumination system. The optical fiber bundles 3 and 4 and other similar optical fiber bundles are located to surround the observation system and each has a flat inwardly inclined exit end face such as shown by 3a and 4a. The illumination optical fiber bundles are arranged at intervals around the observation system to illuminate the object 5 over a wide area.

Figure 1:
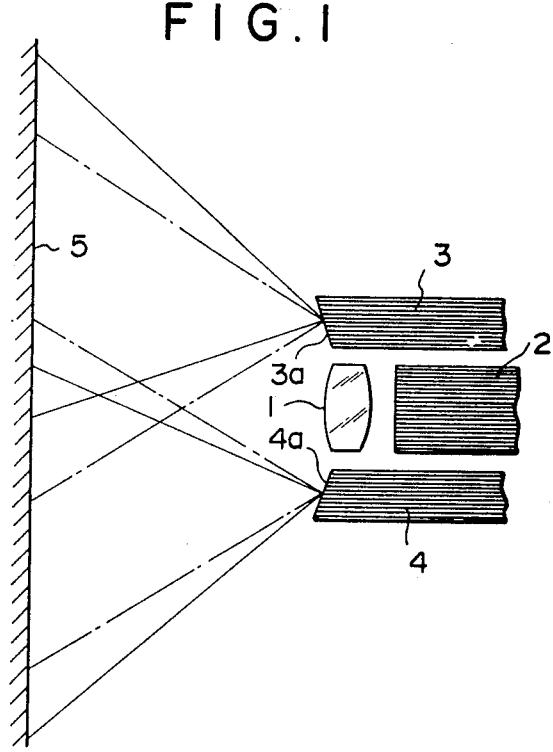
FIG. 1 is a side sectional view showing a part of an optical fiber device employing an illumination system in accordance with an embodiment of the present invention.

In FIG. 1, the cones of light emanating from the exit end faces 3a and 4a of the optical fiber bundles 3 and 4 when the end faces are normal to the axes of the fibers are indicated by chain lines and the cones of light emanating from the end faces 3a and 4a of the optical fiber bundles as shown in the drawing are indicated by solid lines. As shown in FIG. 1 by the chain lines and solid lines, the area illuminated by the light emanating from the end faces 3a and 4a of the fiber bundles 3 and 4 is enlarged by making the end faces inclined inwardly with respect to the plane normal to the axes of fibers. The inclined end faces 3a and 4a are easily obtained by cutting the end of the fiber bundles 3 and 4 by use of a rotary cutter or a grinding wheel.

Figure 2:
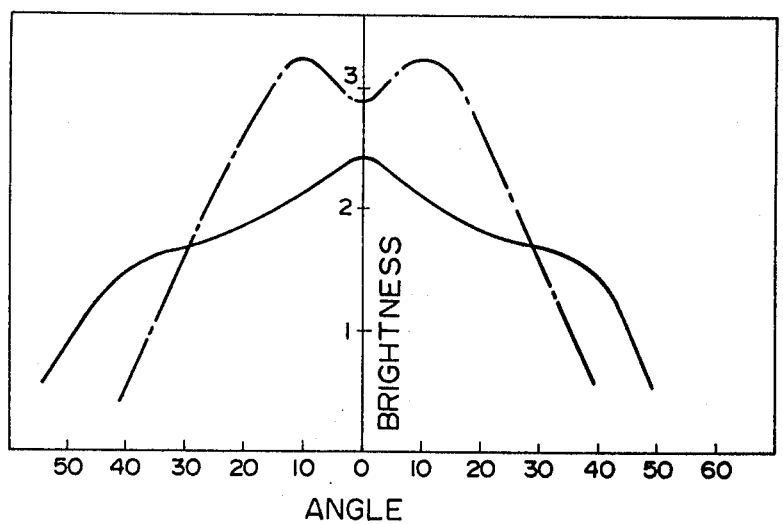
FIG. 2 is a graphical representation showing the distribution of illumination effected by the illumination system in accordance with the embodiment of the present invention as shown in FIG. 1.

The distribution of the illumination is shown in FIG. 2. In FIG. 2, the ordinate represents the brightness on the object and the abscissa represents the angle with respect to the axes of fibers. In FIG. 2 also, the chain line indicates the results in case that the end faces 3a and 4a of the fiber bundles 3 and 4 are normal to the axes and the solid line indicates the results in case that the end faces are inclined in accordance with the present invention.

The angle of inclination of the exit end faces 3a and 4a of the optical fiber bundles 3 and 4 used for illumination with respect to the plane normal to the axes of the fibers is preferred to be 5° to 20°. If the angle of inclination is greater than 20° or smaller than 5°, the loss of light is undesirably increased.

In the above described embodiment the optical fiber bundles 3 and 4 used as the illumination system are in parallel with each other as shown in FIG. 1. However, by making them inclined with respect to the optical axis of the observation system, namely by making them curved or bent outwardly, it is possible to illuminate a larger area of the object 5. The inclination of the fiber bundles 3 and 4 in this case is preferred to be 5° to 10° with respect to the optical axis of the observation system. If the angle of inclination is greater than 10°, or smaller than 5°, the diameter of the fiber assembly becomes impractically large.

The above described embodiment of the invention refers to an optical fiber device in which a plurality of illumination fiber bundles are provided at intervals. Other embodiments relating to an optical fiber device in which a plurality of illumination fiber bundles are provided adjacent to each other will hereinbelow be described with reference to FIGS. 3 to 5.

Figure 3A:
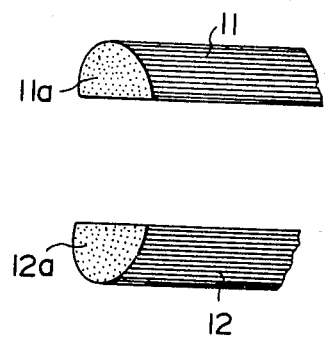
FIG. 3A is a fragmentary perspective view of a pair of optical fiber bundles employed in another embodiment of the invention.
Figure 3B:
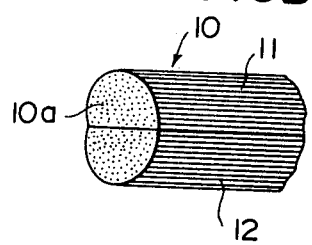
FIG. 3B is a fragmentary perspective view of an optical fiber bundle assembly made of the pair of optical fiber bundles shown in FIG. 3A.

FIGS. 3A and 3B show an embodiment in which a pair of semi-cylindrical fiber bundles 11 and 12 are joined together to form a fiber bundle assembly 10. The end faces 11a and 12a thereof are flat and inclined with respect to a plane normal to the axes of fibers of the bundles. The inclined end faces 11a and 12a are inclined inwardly to give the fiber bundle assembly 10 a V-shaped end face 10a. The light emanating from the end face 10a of the assembly 10 advances outwardly to illuminate a large area on the object to be viewed.

Figure 4:
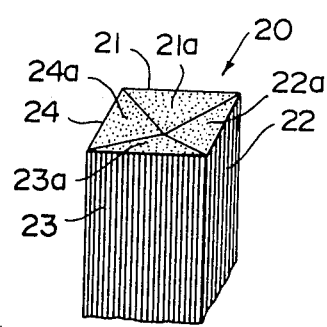
FIG. 4 is a fragmentary perspective view of an optical fiber bundle assembly used as an illumination system in accordance with another embodiment of the present invention.

FIG. 4 shows another embodiment in which four fiber bundles 21, 22, 23 and 24 each having a triangular cross-section are assembled to form a fiber bundle assembly 20. The end faces 21a, 22a, 23a and 24a of the fiber bundles 21 to 24 are flat and inclined inwardly to form a concave end face as a whole. The fiber bundle assembly 20 provides illumination light fluxes expanding in four ways.

Figure 5:
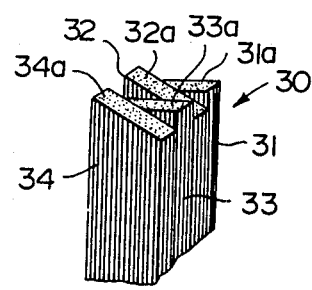
FIG. 5 is a fragmentary perspective view of still another embodiment of the present invention.

FIG. 5 shows still another embodiment of the invention in which four flat fiber bundles 31, 32, 33 and 34 are assembled to form a fiber bundle assembly 30. The end faces 31a, 32a, 33a and 34a of the fiber bundles 31 to 34 are flat and inclined alternately in opposite directions as shown. The fiber bundle assembly 30 provides illumination light fluxes which diverge as a whole.

Figure 6:
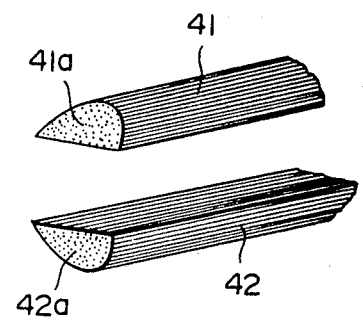
FIG. 6 is a fragmentary perspective view of a pair of optical fiber bundles employed in another embodiment of the invention.
Figure 7:
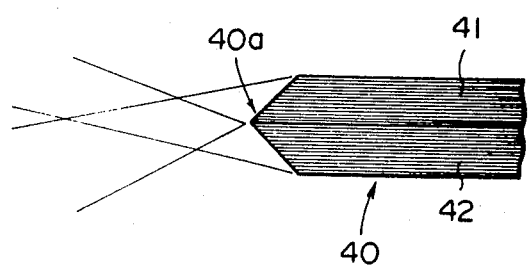
FIG. 7 is a fragmentary side view of an optical fiber bundle assembly made of the pair of optical fiber bundles shown in FIG. 6.

In the embodiment shown in FIGS. 3A and 3B, the pair of semi-cylindrical fiber bundles 11 and 12 have end faces 11a and 12a inclined inwardly to form a negative V-shaped end face 10a. These end faces may be inclined outwardly to form a positive V-shaped end face as shown in FIGS. 6 and 7. Referring to FIG. 6, a pair of fiber bundles 41 and 42 have end faces 41a and 42a inclined outwardly. When these fiber bundles 41 and 42 are joined together to form a fiber bundle assembly 40, the end face 40a thereof becomes a positive V-shaped end face as shown in FIG. 7. With this arrangement also, the light emanating from the end face 40a of the assembly 40 advances finally outwardly to illuminate a large area on the object to be viewed.

The illumination optical fiber bundles of the optical fiber bundle assemblies in accordance with the present invention have flat and inclined exit end faces inclined in different directions to effect a diverging illumination flux as a result. Therefore, the area illuminated is enlarged in accordance with the present invention. Further, since the end faces are simply flat and only inclined, it is easy to manufacture the fiber bundles of the present invention.

We claim:

1. An illumination optical system for an endoscope comprising a plurality of parallel illumination optical fiber bundles located adjacent to a separate image-guide optical fiber bundle which constitutes an observation system having a light-receiving end surface transverse to a first axis, each of said illumination optical fiber bundles having a plurality of light transmitting fibers and a light diverging end face which is in a single plane located at a predetermined angle with respect to said first axis and with respect to its own axis, said end faces of said illumination optical fiber bundles being so constructed and arranged as to diverge light through an area which is in alignment with said first axis and extends beyond the area of said image-guide optical fiber bundle, said end faces of said illumination optical fiber bundles being spaced from said light-receiving end face.

2. An illumination optical system as defined in claim 1 wherein said end faces of the illumination optical fiber bundles are inclined in such directions as to direct the light emanating from the exit end faces outwardly to effect a diverging light flux as a whole.

3. An illumination optical system as defined in claim 1 wherein said illumination optical fiber bundles are semi-cylindrical fiber bundles joined together to make a cylindrical fiber bundle assembly, and said end faces are inclined symmetrically to form a V-shaped end face.

4. An illumination optical system as defined in claim 3 wherein said end faces are inclined inwardly symmetrically to form a negative V-shaped end face.

5. An illumination optical system as defined in claim 3 wherein said end faces are inclined outwardly symmetrically to form a positive V-shaped end face.

6. An illumination optical system as defined in claim 1 wherein said optical fiber bundles have a triangular cross-section and four of the same are joined together to form a fiber bundle assembly having a square cross-section, and said end faces are inclined inwardly symmetrically to form a concave end face.

7. An illumination optical system as defined in claim 1 wherein said optical fiber bundles are flat fiber bundles stacked one on another to make a fiber bundle assembly having a rectangular cross-section, and said end faces are inclined in different directions alternately.

* * * * *